US009574195B2

(12) United States Patent
Parashar et al.

(10) Patent No.: US 9,574,195 B2
(45) Date of Patent: Feb. 21, 2017

(54) RNAI AGENT FOR INHIBITION OF CHIKUNGUNYA VIRUS

(71) Applicant: Indian Council of Medical Research, New Delhi (IN)

(72) Inventors: Deepti Parashar, Pune (IN); Vidya Avinash Arankalle, Pune (IN); Mandar Satish Paingankar, Pune (IN); Satyendra Kumar, Pune (IN); Mangesh Damodar Gokhale, Pune (IN); Sudeep Balan Anakkathil, Pune (IN); Sapna Shinde, Pune (IN)

(73) Assignee: Indian Council of Medical Research, New Delhi (IN)

( * ) Notice: Subject to any disclaimer, the term of this patent is extended or adjusted under 35 U.S.C. 154(b) by 0 days.

(21) Appl. No.: 14/899,135

(22) PCT Filed: Jul. 2, 2014

(86) PCT No.: PCT/IN2014/000441

§ 371 (c)(1),
(2) Date: Dec. 17, 2015

(87) PCT Pub. No.: WO2015/001570

PCT Pub. Date: Jan. 8, 2015

(65) Prior Publication Data

US 2016/0145621 A1 May 26, 2016

(30) Foreign Application Priority Data

Jul. 2, 2013 (IN) .......................... 1960/DEL/2013

(51) Int. Cl.

| | |
|---|---|
| ***C07H 21/02*** | (2006.01) |
| ***C07H 21/04*** | (2006.01) |
| ***C12N 15/113*** | (2010.01) |
| ***A61K 31/713*** | (2006.01) |

(52) U.S. Cl.
CPC ......... *C12N 15/1131* (2013.01); *A61K 31/713* (2013.01); *C12N 2310/14* (2013.01); *C12N 2320/30* (2013.01)

(58) Field of Classification Search
CPC .... A61K 48/00; C12N 15/113; C12N 2310/11
See application file for complete search history.

(56) References Cited

PUBLICATIONS

Mahato et al. (Expert Opinion on Drug Delivery, Jan. 2005, vol. 2, No. 1, pp. 3-28).*
Dash et al., "RNA interference mediated inhibition of Chikungunya virus replication in mammalian cells", Biochemical and Biophysical Research Communications, 2008, vol. 376, pp. 718-722.
Lam et al., "Expression of Plasmid-Based shRNA against the E1 and nsP1 Genes Effectively Silenced Chikungunya Virus Replication", PLOS One, 2012, vol. 7, No. 10, pp. 1-14.
Parashar et al., "RNA interference inhibits Chikungunya virus replication in mammalian cells", available at http://elsevier.conference-services.net/resources/247/2020/pd/ANTI2010_0023.pdf, 2010.
Parashar et al., "Administration of E2 and NS1 siRNAs Inhibit Chikungunya Virus Replication in Vitro and Protects Mice Infected with the Virus", PLOS Neglected Tropical Diseases, 2013, vol. 7, No. 9, pp. 1-15.
Sudeep et al., "Establishment and characterization of a new *Aedes aegypti* (L.) (Diptera: Culicidae) cell line with special emphasis on virus susceptibility", In Vitro Cell.Dev.Biol.-Animal, 2009, vol. 45, pp. 491-495.

* cited by examiner

*Primary Examiner* — Amy Bowman
(74) *Attorney, Agent, or Firm* — The Webb Law Firm

(57) ABSTRACT

Provided herein are RNAi agents for inhibition of Chikungunya virus. The present disclosure provides RNAi agents for inhibition of Chikungunya virus, particularly by targeting the E2 gene and nsP1 gene or both of the Chikungunya virus; the RNAi agents comprising of the entire nucleotide sequence set forth is SEQ ID 1 or SEQ ID 5 or combination thereof; or comprising of 15 or more contiguous nucleotides as set forth is SEQ ID 1 or SEQ ID 5 or combination thereof along with the addition nucleotides from the contiguous region of the E2 and nsP1 target gene. The invention further provides a RNAi composition for reducing the E2 protein and nsP1 protein level of Chikungunya virus and inhibition of Chikungunya virus replication. The combination of RNAi agents provides an excellent therapeutic composition for treatment of Chikungunya virus infection.

9 Claims, 9 Drawing Sheets

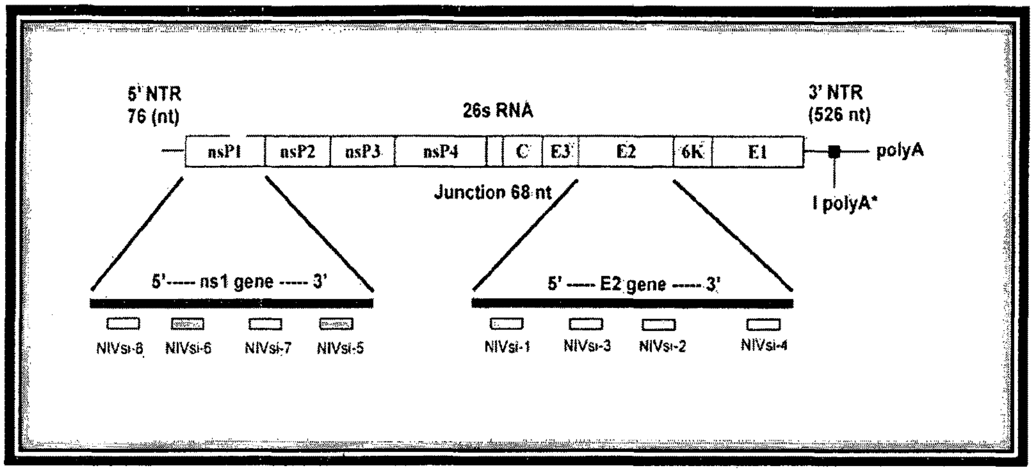
Figure: 1
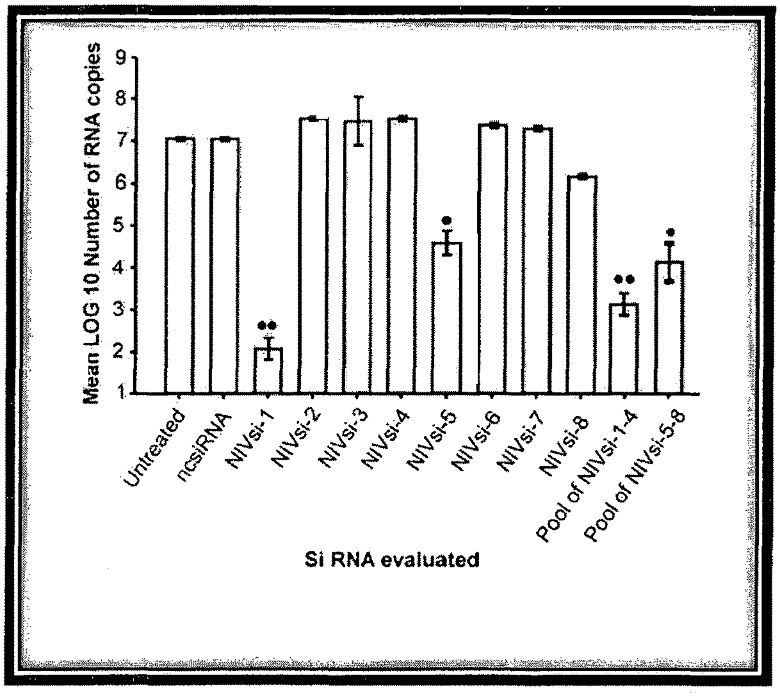
Figure: 2

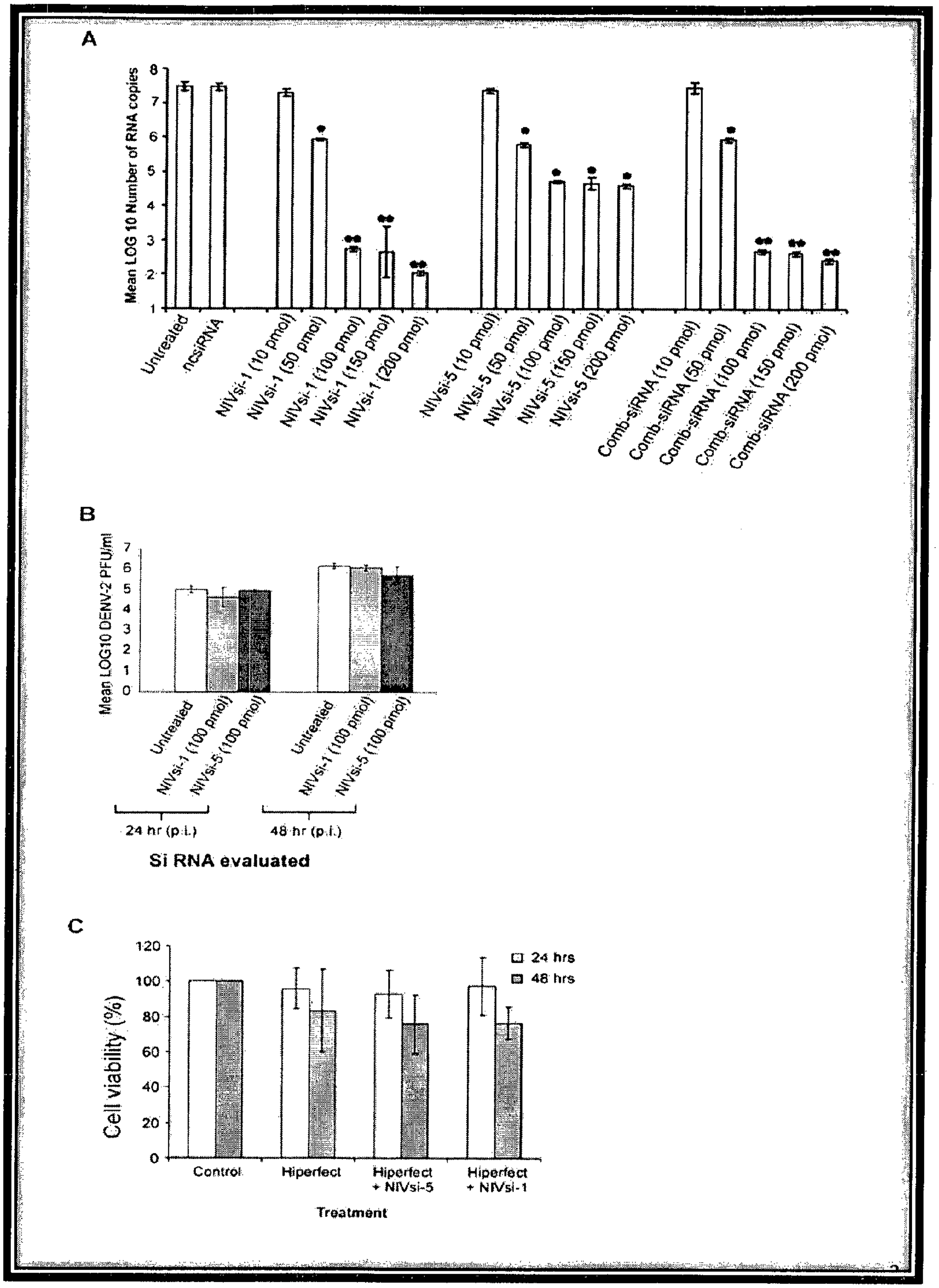
Figure: 3

Figure: 4
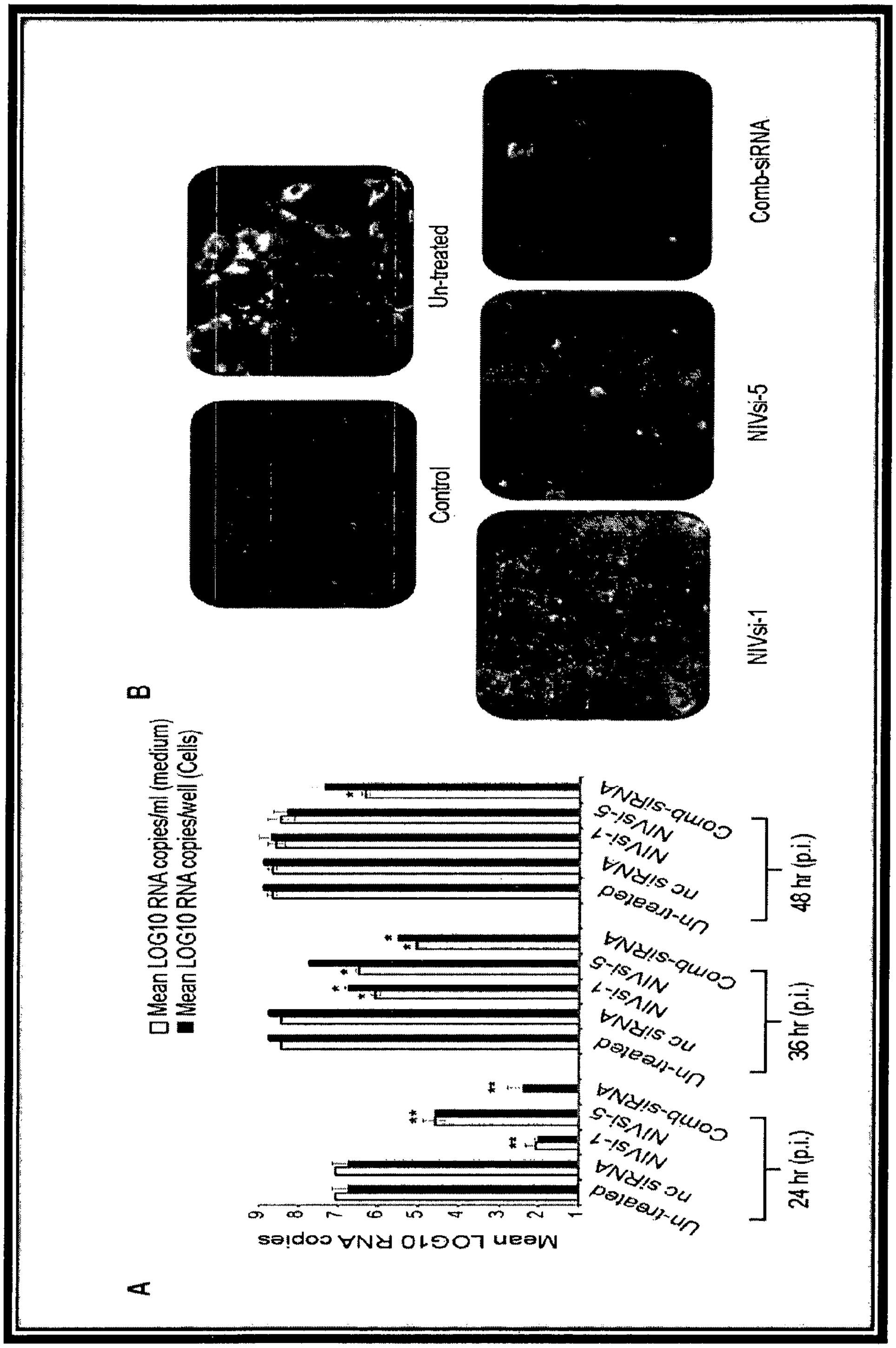

Figure: 5
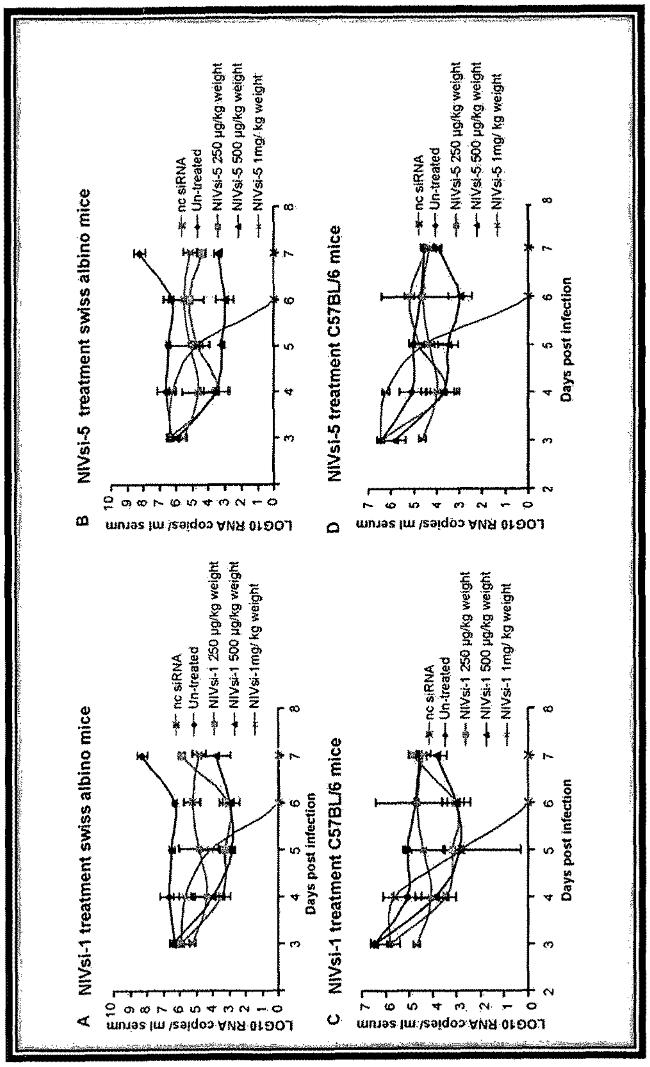

Figure: 6
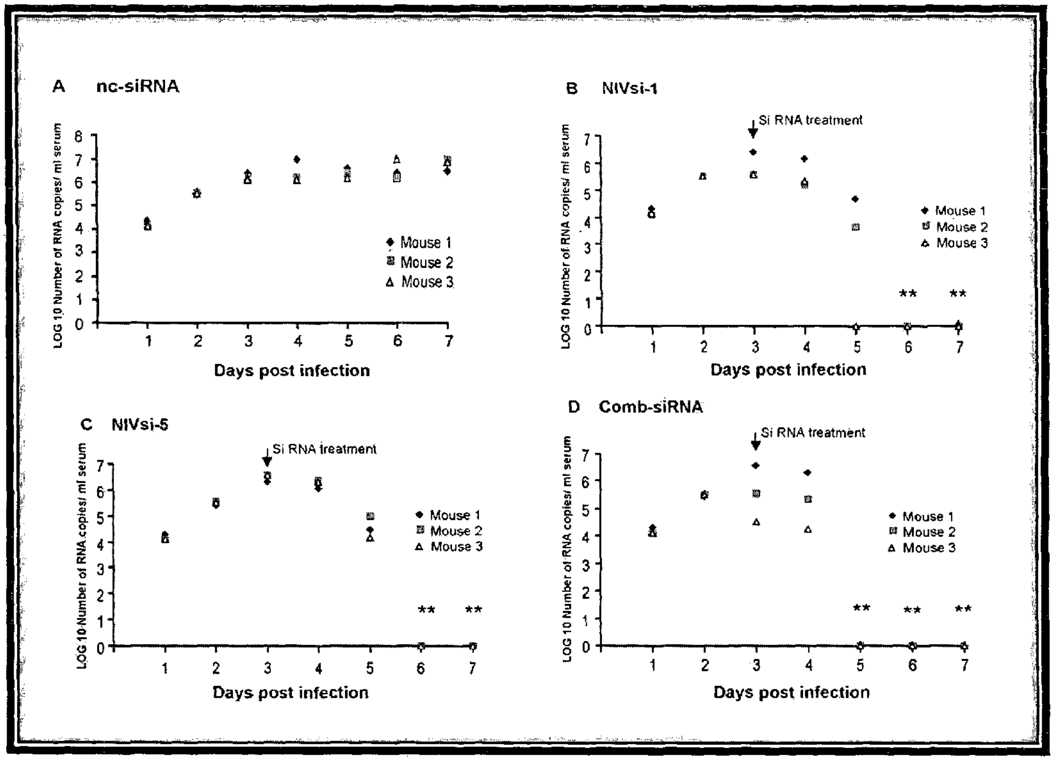

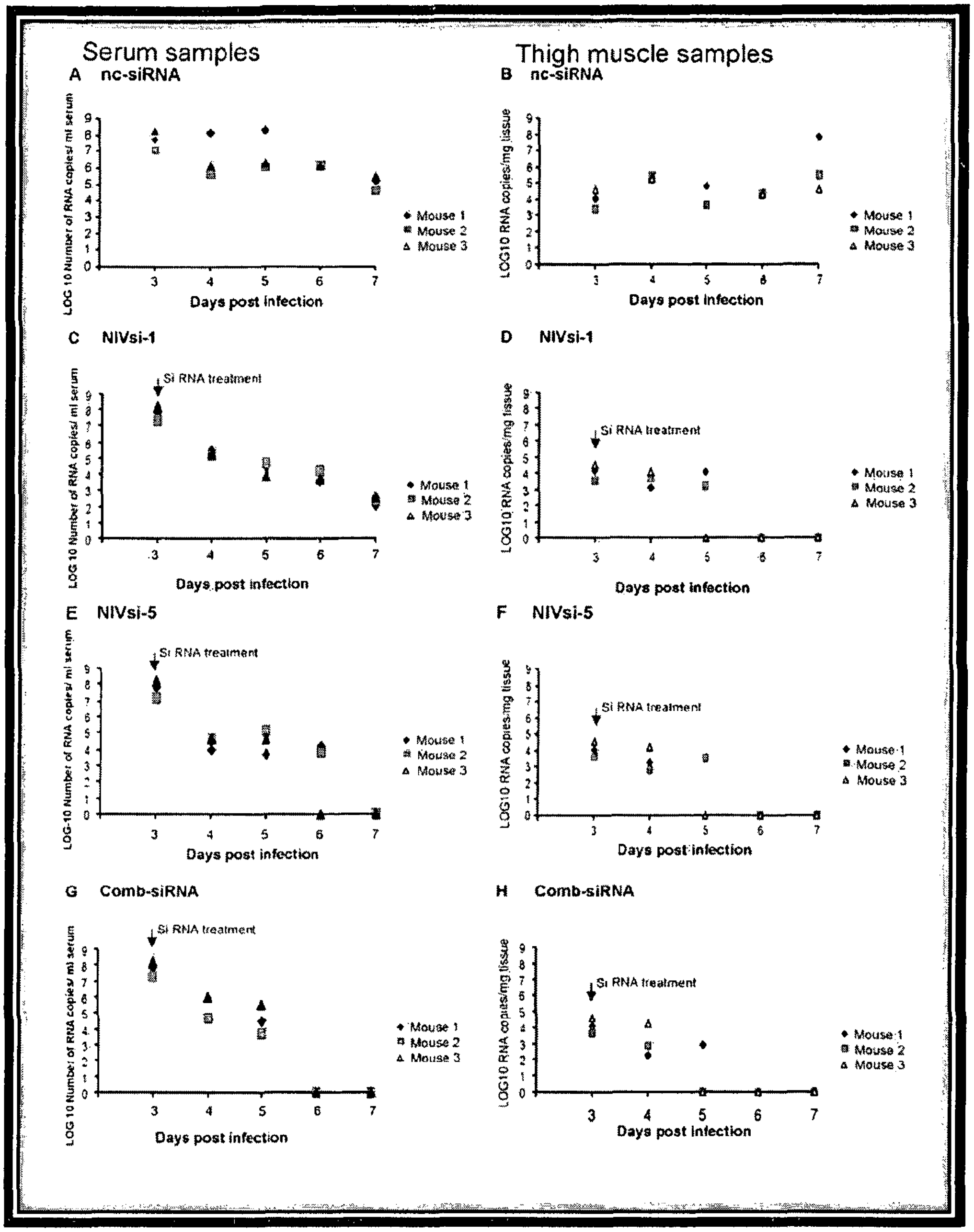
Figure: 7

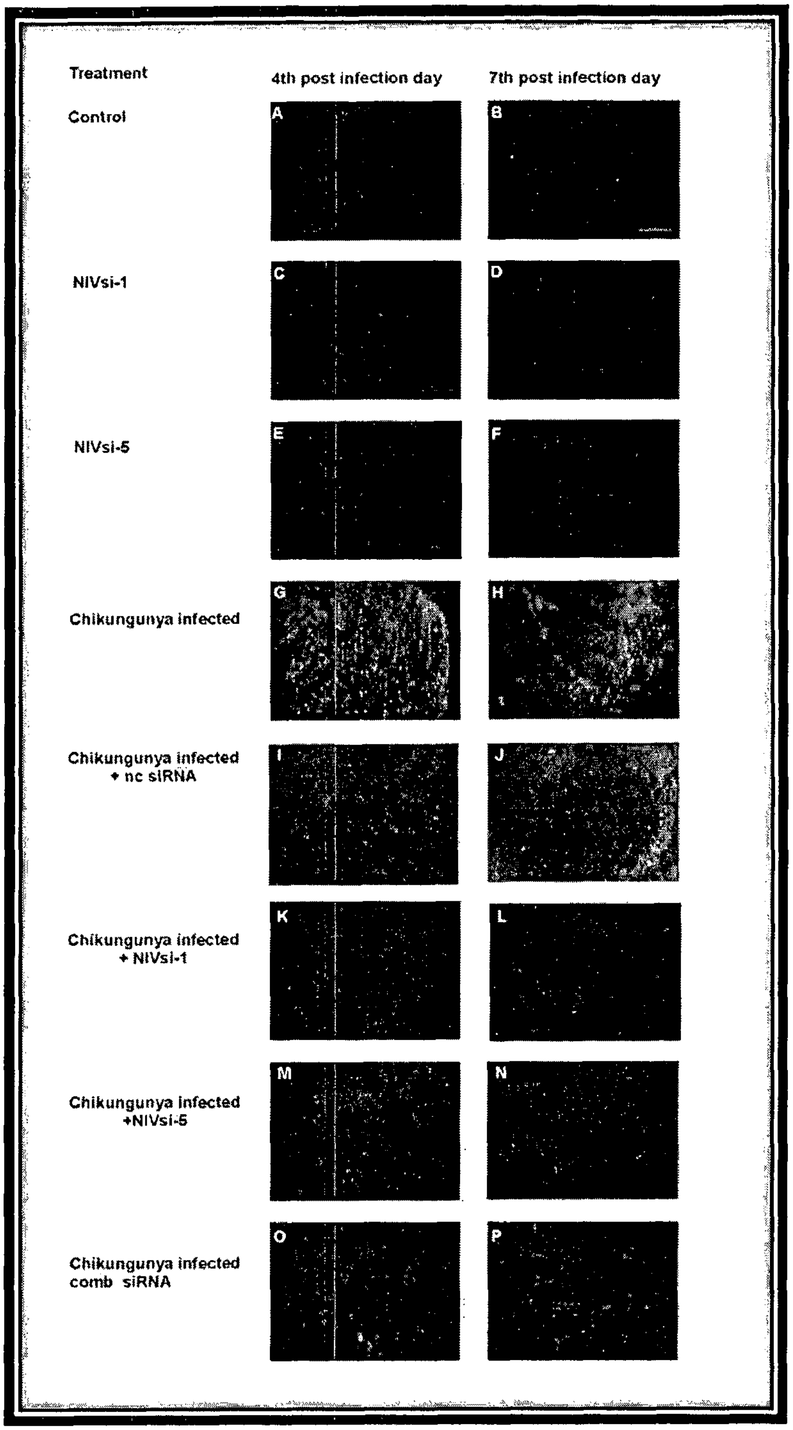
Figure: 8

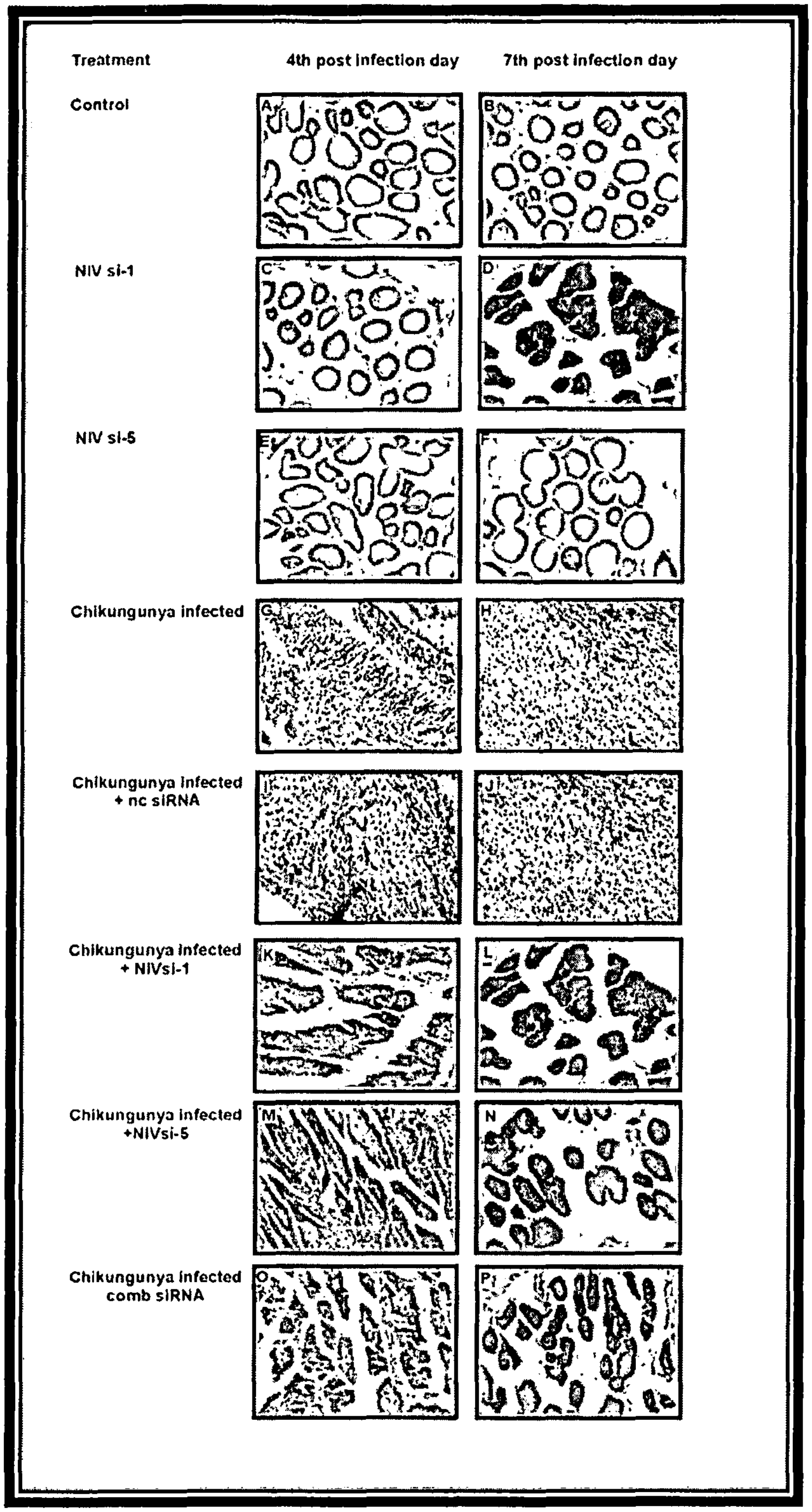
Figure: 9

Nucleotide sequences and IDs of siRNA claimed

| Si RNA Name | Location on genome (nt number) | Location on gene (nt number) | | 5' Sequence 3' |
|---|---|---|---|---|
| SeqID1 NIVsi-1 | 8574-8591 | 30-47 | Sense | r (GGA CAA CUU CAA UGU CUA U) dTdT |
| | | | Antisense | r (AUA GAC AUU GAA GUU GUC C) dTdT |
| SeqID5 NIVsi-5 | 1641-1659 | 1563-1581 | Sense | r (GGU CGA AAU CGA CGU GGA A) dTdT |
| | | | Antisense | r (UUC CAC GUC GAU UUC GAC C) dTdG |

Figure: 10

SEQUENCE LISTING

<160> NUMBER OF SEQ ID NOS: 24

<210> SEQ ID NO 1
<211> LENGTH: 21
<212> TYPE: RNA
<213> ORGANISM: Artificial Sequence
<220> FEATURE:
<223> OTHER INFORMATION: NIVsi-1 Sense
<220> FEATURE:
<221> NAME/KEY: misc_feature
<222> LOCATION: (20)..(21)
<223> OTHER INFORMATION: n is a deoxythymidine

<400> SEQUENCE: 1
ggacaacuuc aaugucuaun n 21

<210> SEQ ID NO 2
<211> LENGTH: 21
<212> TYPE: RNA
<213> ORGANISM: Artificial Sequence
<220> FEATURE:
<223> OTHER INFORMATION: NIVsi-2 Sense
<220> FEATURE:
<221> NAME/KEY: misc_feature
<222> LOCATION: (20)..(21)
<223> OTHER INFORMATION: n is a deoxythymidine

<400> SEQUENCE: 2
ccacgacccu ccugugauan n 21

<210> SEQ ID NO 3
<211> LENGTH: 21
<212> TYPE: RNA
<213> ORGANISM: Artificial Sequence
<220> FEATURE:

<223> OTHER INFORMATION: NIVsi-3 Sense
<220> FEATURE:
<221> NAME/KEY: misc_feature
<222> LOCATION: (20)..(21)
<223> OTHER INFORMATION: n is a deoxythymidine

<400> SEQUENCE: 3
ggaacaaugg gacacuucan n 21

<210> SEQ ID NO 4
<211> LENGTH: 21
<212> TYPE: RNA
<213> ORGANISM: Artificial Sequence
<220> FEATURE:
<223> OTHER INFORMATION: NIVsi-4 Sense
<220> FEATURE:
<221> NAME/KEY: misc_feature
<222> LOCATION: (20)..(21)
<223> OTHER INFORMATION: n is a deoxythymidine

<400> SEQUENCE: 4
ccaccgugac guacgggaan n 21

<210> SEQ ID NO 5
<211> LENGTH: 21
<212> TYPE: RNA
<213> ORGANISM: Artificial Sequence
<220> FEATURE:
<223> OTHER INFORMATION: NIVsi-5 Sense
<220> FEATURE:
<221> NAME/KEY: misc_feature
<222> LOCATION: (20)..(21)
<223> OTHER INFORMATION: n is a deoxythymidine

<400> SEQUENCE: 5
ggucgaaauc gacguggaan n 21

<210> SEQ ID NO 6
<211> LENGTH: 21
<212> TYPE: RNA
<213> ORGANISM: Artificial Sequence
<220> FEATURE:
<223> OTHER INFORMATION: NIVsi-6 Sense
<220> FEATURE:
<221> NAME/KEY: misc_feature
<222> LOCATION: (20)..(21)
<223> OTHER INFORMATION: n is a deoxythymidine

<400> SEQUENCE: 6
ggcuaagaac auaggauuan n 21

<210> SEQ ID NO 7
<211> LENGTH: 21
<212> TYPE: RNA
<213> ORGANISM: Artificial Sequence
<220> FEATURE:
<223> OTHER INFORMATION: NIVsi-7 Sense
<220> FEATURE:
<221> NAME/KEY: misc_feature
<222> LOCATION: (20)..(21)
<223> OTHER INFORMATION: n is a deoxythymidine

<400> SEQUENCE: 7
cggcauccuu gcuacagaan n 21

<210> SEQ ID NO 8
<211> LENGTH: 21
<212> TYPE: RNA
<213> ORGANISM: Artificial Sequence -continued
<220> FEATURE:
<223> OTHER INFORMATION: NIVsi-8 Sense
<220> FEATURE:
<221> NAME/KEY: misc_feature
<222> LOCATION: (20)..(21)
<223> OTHER INFORMATION: n is a deoxythymidine

<400> SEQUENCE: 8
ggaugauguc ggacaggaan n 21

<210> SEQ ID NO 9
<211> LENGTH: 21
<212> TYPE: RNA
<213> ORGANISM: Artificial Sequence
<220> FEATURE:
<223> OTHER INFORMATION: NIVsi-1 Antisense
<220> FEATURE:
<221> NAME/KEY: misc_feature
<222> LOCATION: (20)..(21)
<223> OTHER INFORMATION: n is a deoxythymidine

<400> SEQUENCE: 9
auagacauug aaguuguccn n 21

<210> SEQ ID NO 10
<211> LENGTH: 21
<212> TYPE: RNA
<213> ORGANISM: Artificial Sequence
<220> FEATURE:
<223> OTHER INFORMATION: NIVsi-2 Antisense
<220> FEATURE:
<221> NAME/KEY: misc_feature
<222> LOCATION: (20)..(20)
<223> OTHER INFORMATION: n is a deoxythymidine
<220> FEATURE:
<221> NAME/KEY: misc_feature
<222> LOCATION: (21)..(21)
<223> OTHER INFORMATION: n is a deoxyguanosine

<400> SEQUENCE: 10
uaucacagga gggucguggn n 21

<210> SEQ ID NO 11
<211> LENGTH: 21
<212> TYPE: RNA
<213> ORGANISM: Artificial Sequence
<220> FEATURE:
<223> OTHER INFORMATION: NIVsi-3 Antisense
<220> FEATURE:
<221> NAME/KEY: misc_feature
<222> LOCATION: (20)..(20)
<223> OTHER INFORMATION: n is a deoxyadenosine
<220> FEATURE:
<221> NAME/KEY: misc_feature
<222> LOCATION: (21)..(21)
<223> OTHER INFORMATION: n is a deoxyguanosine

<400> SEQUENCE: 11
ugaagugucc cauuguuccn n 21

<210> SEQ ID NO 12
<211> LENGTH: 21
<212> TYPE: RNA
<213> ORGANISM: Artificial Sequence
<220> FEATURE:
<223> OTHER INFORMATION: NIVsi-4 Antisense
<220> FEATURE:
<221> NAME/KEY: misc_feature
<222> LOCATION: (20)..(21)
<223> OTHER INFORMATION: n is a deoxyguanosine

<400> SEQUENCE: 12
uucccguacg ucacgguggn n 21

<210> SEQ ID NO 13
<211> LENGTH: 21
<212> TYPE: RNA
<213> ORGANISM: Artificial Sequence
<220> FEATURE:
<223> OTHER INFORMATION: NIVsi-5 Antisense
<220> FEATURE:
<221> NAME/KEY: misc_feature
<222> LOCATION: (20)..(20)
<223> OTHER INFORMATION: n is a deoxythymidine
<220> FEATURE:
<221> NAME/KEY: misc_feature
<222> LOCATION: (21)..(21)
<223> OTHER INFORMATION: n is a deoxyguanosine

<400> SEQUENCE: 13
uuccacgucg auuucgaccn n 21

<210> SEQ ID NO 14
<211> LENGTH: 21
<212> TYPE: RNA
<213> ORGANISM: Artificial Sequence
<220> FEATURE:
<223> OTHER INFORMATION: NIVsi-6 Antisense
<220> FEATURE:
<221> NAME/KEY: misc_feature
<222> LOCATION: (20)..(21)
<223> OTHER INFORMATION: n is a deoxythymidine

<400> SEQUENCE: 14
uaauccuaug uucuuagccn n 21

<210> SEQ ID NO 15
<211> LENGTH: 21
<212> TYPE: RNA
<213> ORGANISM: Artificial Sequence
<220> FEATURE:
<223> OTHER INFORMATION: NIVsi-7 Antisense
<220> FEATURE:
<221> NAME/KEY: misc_feature
<222> LOCATION: (20)..(20)
<223> OTHER INFORMATION: n is a deoxyguanosine
<220> FEATURE:
<221> NAME/KEY: misc_feature
<222> LOCATION: (21)..(21)
<223> OTHER INFORMATION: n is a deoxythymidine

<400> SEQUENCE: 15
uucuguagca aggaugccgn n 21

<210> SEQ ID NO 16
<211> LENGTH: 21
<212> TYPE: RNA
<213> ORGANISM: Artificial Sequence
<220> FEATURE:
<223> OTHER INFORMATION: NIVsi-8 Antisense
<220> FEATURE:
<221> NAME/KEY: misc_feature
<222> LOCATION: (20)..(20)
<223> OTHER INFORMATION: n is a deoxythymidine
<220> FEATURE:
<221> NAME/KEY: misc_feature
<222> LOCATION: (21)..(21)
<223> OTHER INFORMATION: n is a deoxycytidine

<400> SEQUENCE: 16
uuccuguccg acaucauccn n 21

-continued

<210> SEQ ID NO 17
<211> LENGTH: 24
<212> TYPE: DNA
<213> ORGANISM: Artificial Sequence
<220> FEATURE:
<223> OTHER INFORMATION: actin primer

<400> SEQUENCE: 17
ggccgaggac tttgattgca catt 24

<210> SEQ ID NO 18
<211> LENGTH: 24
<212> TYPE: DNA
<213> ORGANISM: Artificial Sequence
<220> FEATURE:
<223> OTHER INFORMATION: actin primer

<400> SEQUENCE: 18
aggatggcaa gggacttcct gtaa 24

<210> SEQ ID NO 19
<211> LENGTH: 24
<212> TYPE: DNA
<213> ORGANISM: Artificial Sequence
<220> FEATURE:
<223> OTHER INFORMATION: IFN-alpha primer

<400> SEQUENCE: 19
aggaggagtt tgatggcaac cagt 24

<210> SEQ ID NO 20
<211> LENGTH: 24
<212> TYPE: DNA
<213> ORGANISM: Artificial Sequence
<220> FEATURE:
<223> OTHER INFORMATION: IFN-alpha primer

<400> SEQUENCE: 20
tcctcatccc aagcagcaga tgaa 24

<210> SEQ ID NO 21
<211> LENGTH: 24
<212> TYPE: DNA
<213> ORGANISM: Artificial Sequence
<220> FEATURE:
<223> OTHER INFORMATION: IFN-beta primer

<400> SEQUENCE: 21
tgtggcaatt gaatgggagg cttg 24

<210> SEQ ID NO 22
<211> LENGTH: 24
<212> TYPE: DNA
<213> ORGANISM: Artificial Sequence
<220> FEATURE:
<223> OTHER INFORMATION: IFN-beta primer

<400> SEQUENCE: 22
tctcatagat ggtcaatgcg gcgt 24

<210> SEQ ID NO 23
<211> LENGTH: 24
<212> TYPE: DNA
<213> ORGANISM: Artificial Sequence
<220> FEATURE:

-continued

```
<223> OTHER INFORMATION: IFN-gamma primer

<400> SEQUENCE: 23

agcggctgac tgaactcaga ttgt                                              24


<210> SEQ ID NO 24
<211> LENGTH: 24
<212> TYPE: DNA
<213> ORGANISM: Artificial Sequence
<220> FEATURE:
<223> OTHER INFORMATION: IFN-gamma primer

<400> SEQUENCE: 24

actgctttct ttcagggaca gcct                                              24
```

RNAI AGENT FOR INHIBITION OF CHIKUNGUNYA VIRUS

CROSS-REFERENCE TO RELATED APPLICATIONS

This application is the United States national phase of International Application No. PCT/IN2014/000441 filed Jul. 2, 2014, and claims priority to Indian Patent Application No. 1960/DEL/2013 filed Jul. 2, 2013, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1511224_ST25.txt. The size of the text file is 6,531 bytes, and the text file was created on Jun. 24, 2016.

FIELD OF THE INVENTION

The invention relates to an RNA interference (RNAi) agent and its use for inhibition of Chikungunya virus in mammals. The invention further relates to the RNAi based therapeutic strategy for controlling Chikungunya virus infection.

BACKGROUND OF THE INVENTION

Alphaviruses contains a linear, positive sense, single stranded RNA genome of approximately 11.8 kb. Their RNA genome consists of a capped 5' non-coding region (NCR) and 3' polyadenylated NCR. The non-structural proteins i.e. nsP1, nsP2, nsP3 & nsP4 are required for virus replication whereas structural proteins i.e. E1, E2, E3 and 6K forms part of capsid and envelope. Given the similarity of Chikungunya virus genomic structure with those of other alphaviruses, Chikungunya virus is expected to encode spikes on the virion surface that is each formed by the three E1-E2 heterodimers; where E1 glycoprotein mediates fusion and the E2 glycoprotein interact with the host receptor. These structural and non-structural proteins are critical for the entry and multiplication of alpha-virus in the host cell and therefore represent rational targets for antiviral therapy.

RNA interference (RNAi) is the process of sequence specific Post Transcriptional Gene Silencing (PTGS) in Eukaryotes. In RNAi, long dsRNA and miRNA precursors are processed to small interfering RNA (siRNA)/microRNA duplexes by the RNaseIII-like enzyme Dicer. The siRNA/miRNA duplexes thus formed then binds with other components in cell to form a nucleic acid-protein complex called RNA-induced silencing complex (RISC). The activated RISC targets a homologous mRNA by base pairing, resulting in the cleavage and degradation of the mRNA inhibiting cell-specific gene expression. In eukaryotes, RNAi not only regulates the gene expression but also acts as a cellular defence mechanism against invaders including viruses like Poliovirus, HIV, Hepatitis, Chikungunya etc. In recent years inhibition of specific genes by RNAi has proven to be a potential therapeutic strategy against viral infections. For instance, inhibition of virus replication and gene expression by directly introducing RNAi agents into the cells have been reported for several RNA viruses including several important human pathogens such as HIV, Hepatitis, Influenza virus etc. It has also been shown that alphaviruses such as Selmiki Forest Virus, Venezuelan equine encephalitis are susceptible to RNAi action.

Chikungunya virus is a mosquito transmitted alpha-virus belonging to family Togaviridae. Chikungunya virus is responsible for an acute infection characterized by high fever, arthralgia, myalgia, headache, rash etc. Although of immense medical importance, no effective, vaccine or specific therapy is available.

Dash et al in 'RNA interference mediated inhibition of Chikungunya virus replication in mammalian cells'; Biochemical and Biophysical Research Communications; September 2008] have demonstrated that introduction of exogenous siRNA can inhibit replication of Chikungunya virus in-vitro. However, success of this study is limited as siRNAs used against ns3 and E1 genes of Chikungunya virus were shown to reduce replication by 65% by 48 h post infection and not evaluated in-vivo. Also, Lam et al in 'Expression of Plasmid-Based shRNA against the E1 and nsP1 Genes Effectively Silenced Chikungunya virus replication'; PLOS ONE; October 2012 have demonstrated the effective anti-viral strategy against Chikungunya virus infection in-vitro & in-vivo, targeting E1 and nsP1 genes using shRNA.

These results indicate the potential use of novel strategies using RNAi against the structural and non structural proteins of alphaviruses. E2 and nsP1 genes are highly conserved in Chikungunya virus strains and are important in entry and multiplication in host cell and, therefore, represent rational targets for antiviral therapy i.e. inhibition of Chikungunya virus.

OBJECTS OF THE INVENTION

It is therefore an object of this invention to develop a RNAi agent for the inhibition of Chikungunya virus, in vitro or/and in vivo.

It is a further of the invention to develop an RNAi agent for the inhibition of E2 gene and nsP1 gene of Chikungunya virus.

A further object of this invention to develop a RNAi agent for the inhibition of E2 and nsP1 gene of Chikungunya virus, resulting in decreased levels of viral proteins, viral mRNA or viral titers of Chikungunya virus.

A still further object of this invention is to develop an RNAi agent for preparing a composition for the inhibition of E2 gene and nsP1 gene of Chikungunya virus.

Yet another object of the invention is to develop an RNAi agent for use in a method for inhibition of Chikungunya virus using RNAi.

SUMMARY OF THE INVENTION

According to this invention there is provided a novel siRNAs targeted against structural and non-structural proteins of Chikungunya virus for inhibition of the said proteins. The present invention relates to the potential use of siRNA in silencing of sequence specific genes of Chikungunya virus and thus helps in designs of novel therapeutic strategy for controlling the Chikungunya virus infection and transmission. More particularly, invention relates to the efficient use of siRNA targeted again E2 and nsP1 genes individually and in combination in inhibiting the replication of Chikungunya virus in-vitro and in-vivo.

BRIEF DESCRIPTION OF THE DRAWINGS

FIG. 1 Schematic representation of the sites of the eight siRNA target sequence in Chikungunya virus genome FIG. 2 Effect of different siRNAs on production of Chikungunya virus FIG. 3 Optimization of siRNA concentration:

A) Efficiency of different siRNAs in reducing Chikungunya virus replication in-vitro B) Effect of siRNAs on Dengue virus-2 growth C) Cell viability after siRNA treatment (MTT assay)

FIG. 4 Evaluation of siRNAs directed against Chikungunya virus E2 and nsP1:

A) Quantitative analysis of intra cellular and extra cellular Chikungunya virus RNA copies using real time PCR B) Detection of Chikungunya virus in Vero E6 cells using immuno-fluorescence microscopy FIG. 5 Dose dependent reduction in Chikungunya virus copies/ml serum after injection with siRNA NIVsi-1 and NIVsi-5 in swiss albino and C57BL/6 mice infected with Chikungunya virus: Swiss albino and C57BL/6 mice were infected with Chikungunya virus i.v. ($1\times10^6$ PFU Chikungunya virus; 100 μl of $10^7$ pfu/ml). After 72 h of post infection Swiss albino mice were inoculated i.v. with A) ncsiRNA (siRNA against Chandipura virus), 250 μg, 500 μg and 1 mg/kg body weight NIVsi-1 siRNA (n=3 in each treatment and time point), B) ncsiRNA, 250 μg, 500 μg and 1 mg/kg body weight NIVsi-5 siRNA (n=3 in each treatment and time point). After 72 h of post infection C57BL/6 mice were inoculated i.v. with C) ncsiRNA, 250 μg, 500 μg and 1 mg/kg body weight NIVsi-1 siRNA (n=3 in each treatment and time point), D) ncsiRNA, 250 μg, 500 μg and 1 mg/kg body weight NIVsi-5 siRNA (n=3 in each treatment and time point). At indicated time after injection of siRNA blood was collected from eye and RNA was isolated from serum. Chikungunya virus E3 RNA copies were quantitated using real time RT-PCR. Values are given as $LOG_{10}$ RNA copies/ml serum.

FIG. 6 The reduction in Chikungunya virus copies/ml serum after injection with siRNA NIVsi-1 and NIVsi-5 in Swiss albino mice infected with Chikungunya virus:

A) ncsiRNA 1 mg/kg body weight

B) 1 mg/kg body weight NIVsi-1 (n=3),

C) 1 mg/kg body weight NIVsi-5 (n=3) and

D) Combination of NIVsi-1 and NIVsi-5 (n=3) 1 mg/kg body weight each

FIG. 7 The reduction in Chikungunya virus copies/ml serum after injection with siRNA NIVsi-1 and NIVsi-5 in C57BU6 mice infected with Chikungunya virus: C57BL/6 mice (n=15) were infected with Chikungunya virus i.v. ($1\times10^6$ PFU Chikungunya virus; 100 μl of $10^7$ pfu/ml) and viral RNA copies were checked in serum and muscle tissues. After 72 h of post infection mice were inoculated i.v. with 1 mg/kg body weight nc siRNA (FIGS. 7A, 7B), 1 mg/kg body weight NIVsi-1 (n=15) (FIGS. 7C and 7D), 1 mg/kg body weight NIVsi-5 (n=15) (FIGS. 7E and 7F) and combination of NIVsi-1 and NIVsi-5 (n=15) 1 mg/kg body weight each (FIGS. 7G and 7H) and viral RNA copies were checked in serum and muscle tissues at indicated time after injection. Chikungunya virus E3 RNA was quantitated using real time RT-PCR. Values are given as $Log_{10}$ RNA copies/ml serum and $Log_{10}$ RNA copies/mg of tissue. Significance Dunnett's test: *$p<0.05$; **$p<0.01$.

FIG. 8 Detection of Chikungunya in mouse muscle tissues using Immuno-fluorescence assay after Chikungunya infection and siRNA treatment: C57BL/6 mice were infected with Chikungunya virus i.v. ($1\times10^6$ PFU Chikungunya virus: 100 μl of $10^7$ pfu/ml). PBS, ncsiRNA, E2 siRNA and ns1 siRNA injected mice showed absence of chikungunya antigen at $4^{th}$ and $7^{th}$ PID (A, B, C, D, E and F). Chikungunya virus infected muscles showed presence of Chikungunya antigen (G and H), ncsiRNA treated Chikungunya virus infected muscles showed presence of chikungunya antigen (I and J) whereas siRNA treated Chikungunya virus infected mice muscle tissues showed the faint staining of Chikungunya antigen (K, L, M, N, O and P) (Magnification ×200).

FIG. 9 Histopathological changes in mouse muscle tissues after Chikungunya infection and siRNA treatment: C57BL/6 mice were infected with Chikungunya virus i.v. ($1\times10^6$ PFU Chikungunya virus; 100 μl of $10^7$ pfu/ml). Hematoxylin/eosin-stained tissue sections were screened to investigate the pathological effects of siRNA treatment. PBS injected mice showed normal cellular organization (A and B). No significant cellular changes were observed in E2 siRNA treated mice (C and D) and nsP1 siRNA treated mice (E and F). Chikungunya virus infected muscles showed pronounced monocyte/macrophage infiltrates, necrosis and edema {G and H), nc siRNA treated Chikungunya virus infected muscles showed pronounced monocyte/macrophage infiltrates, necrosis and edema (I and J) whereas siRNA treated Chikungunya virus infected mice muscle tissues showed the regeneration after treatment (K, L, M, N, O and P) (Magnification ×400).

FIG. 10 Nucleotide sequences and IDs of siRNA claimed: Sense (SeqID 1 and SeqID 5) and antisense (SeqID 9 and SeqID 13) sequences are shown.

DETAILED DESCRIPTION

Thus according to this invention is provided an RNAi agent for the inhibition of Chikungunya virus in mammals. An "RNA agent" as used herein, is an unmodified RNA, modified RNA, or nucleoside surrogates, all of which are described herein or are well known in the RNA synthetic art. While numerous modified RNAs and nucleoside surrogates are described, preferred examples include those which have greater resistance to nuclease degradation than do unmodified RNAs.

An "RNAi agent" (abbreviation for "RNA interfering agent") as used herein, is an RNA agent, which can down-regulate the expression of a target gene, e.g., Chikungunya virus gene. While not wishing to be bound by theory, an RNAi agent may act by one or more of a number of mechanisms, including post-transcriptional cleavage of a target mRNA sometimes referred to in the art as RNAi, or post-transcriptional or pre-translational mechanisms. An RNAi agent can be a double stranded (ds) RNAi agent. The RNAi described herein can be a microRNA (miRNA), short hairpin RNA (shRNA), or small interfering RNA (siRNA).

A "subject" as used herein, is an animal, more preferably a mammal, undergoing treatment for the disorder mediated by Chikungunya virus infection. The subject can be any mammal e.g. a primate, monkey, mouse, human etc.

A "cell or cell-line" used herein is a mammalian cell line which can be infected with Chikungunya virus. The example of Cell line includes Vero E6 cell line.

"Treatment" used herein refers to amelioration of any biological or pathological condition mediated by the viral infection or the reduction of viral gene products present.

MTT assay as used herein is a colorimetric assay for measuring the activity of cellular enzymes that reduce the tetrazolium dye, MTT (3-(4,5-Dimethylthiazol-2-yl)-2,5-diphenyltetrazolium bromide, a yellow tetrazole). Tetrazolium dye assays are used to measure cytotoxicity (loss of viable cells) or cytostatic activity (shift from proliferative to resting status) of potential medicinal agents and toxic materials.

Plaque Assay as used herein is the standard method used to determine virus concentration in terms of infectious dose. Viral plaque assays determine the number of plaque forming units (pfu) in a virus sample, which is one measure of virus quantity. This assay is based on a microbiological method conducted in petri dishes or multi-well plates.

Immunofluorescence (IFA) as used herein is a technique used for light microscopy with a fluorescence microscope is used primarily on microbiological samples. This technique uses the specificity of antibodies to their antigen to target fluorescent dyes to specific biomolecules targets within a cell, and therefore allows visualisation of the distribution of the target molecule through the sample. IFA is a widely used example of immune staining and is a specific example of immunohistochemistry that makes use of fluorophores to visualise the location of the antibodies. IFA can be used on tissue sections, cultured cell lines, or individual cells, and may be used to analyse the distribution of proteins, glycans, and small biological and non-biological molecules.

Design and Selection of RNAi Agent:

The present invention is based on demonstration of targeted gene silencing of Chikungunya viral gene in vitro as well as in vivo following administration of RNAi agent resulting in reduced titer of Chikungunya virus and treatment of Chikungunya viral infection.

According to described embodiments, all Chikungunya Virus whole genotype sequences were retrieved from GenBank NCBI database (https://www.ncbi.nlm.nih.gov/) were used for the designing of the RNAi agent. The required sequence information was retrieved from NCBI. All the sequences were first aligned using the MUSCLE software and the consensus sequences were derived which were further used for designing of RNAi agents. The RNAi agents i.e. siRNAs were designed using the HP Onguard siRNA design. RNAi agents i.e. siRNAs were synthesized (Qiagen, Germany) and checked for homology to all other sequences of the genome using non-redundant sequence database and homology analysis tool. In all the RNAi experiments described herein, RNAi agent or siRNA i.e. negative control siRNA (ncsiRNA) without significant homology with known mammalian genes was used as non silencing control.

In one of the embodiments, RNAi agent were designed and synthesized for the inhibition of E2 gene of Chikungunya virus according to the above described procedure. [Table 1, FIG. 1, Seq ID 1-Seq ID 4].

In other Embodiment, RNAi agents were designed and synthesized for the Inhibition of nsP1 genes of Chikungunya virus according to the above described procedure [Table 1, FIG. 1, Seq ID 5-Seq ID 8].

Based on these results, the invention specifically provides an RNAi agent that can be used in treatment of Chikungunya viral infection, in isolated form or as a pharmaceutical composition described below. Such agents will include sense strand having at least 15 or more contiguous nucleotide sequences that are complementary to the Chikungunya virus genes and an antisense strand having at least 15 or more contiguous nucleotides that are complementary to the sense strand. Particularly useful are RNAi agents that consist of, consist essentially of or comprise a partial nucleotide sequence from the E2 and nsP1 genes of Chikungunya virus as provided in Table 1.

The RNAi agents of the present invention are based on and comprise at least 15 or more contiguous nucleotides from one of the RNAi agents shown in Table 1. In such agents, consist essentially of or comprise the entire sequence provided in table or can comprise 15 or more contiguous nucleotides provided in Table 1 along with additional nucleotides from the contiguous region of the target genes.

The RNAi agent can be rationally designed based on the sequence information and desired characteristics and the information provided in Table 1. The RNAi agent can be designed according to the sequence of the agents provided in the tables as well as in view of the entire coding sequence of the target gene.

Accordingly, the present invention provides RNAi agents comprising a sense strand and antisense strand each comprising a sequence of at least 15, 16, 17, 18, 19, 20, 21, 22 or 23 nucleotides which is essentially identical to, as defined above, a portion of gene from a Chikungunya virus, particularly the E2 or nsP1 genes of Chikungunya virus. Exemplified RNAi agents include those that comprise 15 or more contiguous nucleotides from one of the agents provided in Table 1. The double stranded portion of RNAi agent can be equal to or at least 15 to 23 nucleotide bp in length.

The agents provided in the Table 1 are 21 nucleotides in length. The RNAi agent contains a 19 nucleotide double stranded region with 2 nucleotide overhang on each of the 3' region. These agents can be modified as described herein to obtain equivalent agents comprising at least a portion of these sequences (15 or more contiguous nucleotides) and or modifications to oligonucleotide bases or linkages.

Generally the RNAi agents of the invention include a region of sufficient complementarity to the viral genes e.g. the E2 or nsP1 gene of Chikungunya virus, and are of sufficient length in terms of nucleotides, that the RNAi agent, or a fragment thereof, can mediate down regulation of the specific viral gene. The antisense strands of RNAi agents of the present invention are preferably fully complementary to the mRNA sequence of the viral genes, as herein for the E2 and nsP1 proteins of Chikungunya virus. However, there may not be perfect complementarity between the RNAi agent and the target, but correspondence must be sufficient to enable the RNAi agent or a cleavage product thereof, to direct sequence specific silencing, e.g. by RNAi cleavage of an Chikungunya virus mRNA.

Therefore, the RNAi agents of the invention includes agents comprising a sense strand and antisense strand each comprising a sequence of at least 15, 16, 17, 18 or 19 nucleotides which is essentially identical, as defined below to one of the sequences of the viral gene, particularly the E2 and nsP1 gene of Chikungunya virus, such as those provided in Table 1, except that not more than 1, 2, or 3 nucleotides per strands respectively, have been substituted by other nucleotides (e.g. adenosine replaced by uracil), while essentially replacing the ability to interfere with the Chikungunya virus gene expression in cultured mammalian cells, as defined herein. These agents therefore may possess 1, 2 or 3 mismatched nucleotides along with 15 or more nucleotides identical to one of the targeted mRNA sequences of Chikungunya virus.

Mismatches to the target viral mRNA sequence, particularly in the antisense strand are mostly tolerated in the terminal regions and if present are preferably in the terminal region or regions, more preferably within the 6, 5, 4, or 3 nucleotides of a 5' and or 3' terminus, most preferably within 6, 5, 4, or 3 nucleotides of a 5' terminus of a sense strand or the 3' end of antisense strand. The sense strand need only be sufficiently complementary with the antisense strand to maintain the overall double stranded character of the molecule. The siRNA agents may have single stranded overhangs, preferably the 3' overhangs, of 1 to 4 nucleotides, in length, on one or both ends of the RNAi agent. These overhangs are important in stability of the RNAi agent and its secondary structure so in the present invention according to sequence dA or dT were used in the overhang region.

It is preferred that the sense strand and the antisense strand be chosen that an RNAi agent includes a single strand or unpaired region at one or both ends of the molecule, such as those exemplified in Table 1. Thus, an RNAi agent contains sense and antisense strands, preferably paired to contain an overhang, e.g. 5' or 3' overhang of 2 to 3 nucleotides, preferably 3' overhangs.

Preferred lengths for the duplex region is between 15 to 30, more preferably 18, 19, 20, 21 or 22 nucleotides in length, most preferably 21 nucleotides in length. Hairpin and other RNA molecules which provide the required double stranded region, and preferably a 3' overhang are also within the scope of this invention.

acceptable carriers and excipients suitable for administration in humans. The RNAi delivery agent can also be any suitable transfection agent known in the art, example Hiperfect Transfection kit available in the market.

The RNAi agent formulation can contain one or more than one RNAi agents targeted against different target sites of the same gene or different genes of the virus. The different RNAi agents can also target different genes of one or more viruses.

TABLE 1

Nucleotide sequences of siRNA designed for Chikungunya virus genes

| Si RNA Name | Location on genome (nt number) | Location on gene (nt number) | 5' Sequence 3' |
|---|---|---|---|
| siRNA targeted against E2 Gene of Chikungunya Virus | | | |
| SeqID 1<br>NIVsi-1<br>Seq ID 9 | 8574-8591 | 30-47 | Sense r(GGA CAA CUU CAA UGU CUA U) dTdT<br>Antisense r(AUA GAC AUU GAA GUU GUC C) dTdT |
| Seq D 2<br>NIVsi-2<br>Seq ID 10 | 8955-8973 | 411-429 | Sense r(CCA CGA CCC UCC UGU GAU A) dTdT<br>Antisense r(UAU CAC AGG AGG GUC GUG G) dTdG |
| SeqID 3<br>NIVsi-3<br>Seq ID 11 | 8848-8866 | 304-322 | Sense r(GGA ACA AUG GGA CAC UUC A) dTdT<br>Antisense r(UGA AGU GUC CCA UUG UUC C) dAdG |
| SeqID 4<br>NIVsi-4<br>Seq ID 12 | 9386-9404 | 842-860 | Sense r(CCA CCG UGA CGU ACG GGA A) dTdT<br>Antisense r(UUC CCG UAC GUC ACG GUG G) dGdG |
| siRNA targeted against nsP1 Gene of Chikungunya Virus | | | |
| SeqID 5<br>NIVsi-5<br>Seq ID 13 | 1641-1659 | 1563-1581 | Sense r(GGU CGA AAU CGA CGU GGA A) dTdT<br>Antisense r(UUC CAC GUC GAU UUC GAC C) dTdG |
| SeqID 6<br>NIVsi-6<br>Seq ID 14 | 695-713 | 617-635 | Sense r(GGC UAA GAA CAU AGG AUU A) dTdT<br>Antisense r(UAA UCC UAU GUU CUU AGC C) dTdT |
| SeqID 7<br>NIVsi-7<br>Seq ID 15 | 1107-1125 | 1029-1047 | Sense r (CGG CAU CCU UGC UAC AGA A) dTdT<br>Antisense r(UUC UGU AGC AAG GAU GCC G) dGdT |
| SeqID 8<br>NIVsi-8<br>Seq ID 16 | 290-308 | 212-230 | Sense r(GGA UGA UGU CGG ACA GGA A) dTdT<br>Antisense r(UUC CUG UCC GAC AUC AUC C) dTdC |

Composition Comprising the RNAi Agent:

The RNAi agent described herein, can be formulated for administration to a subject, preferably administration to a mammal via parenteral or any other suitable route. The delivery agents can be customized according to the route of administration of the RNAi agent.

In one of the embodiments, the RNAi agents i.e. NIVsi-1 and NIVsi-5 individually and in combination were mixed with Hiperfect Transfection reagent to form a composition, which was used for the inhibition of the Chikungunya virus in mammalian models.

The formulated RNAi agent can be administered in combination with any other suitable delivery agents e.g., delivery agents can be a therapeutic agent or any other agent which stabilizes an RNAi agent e.g., a protein that complex with the RNAi agent to form an iRNP. The RNAi agent can be formulated into liquid composition by mixing it with sterile water. The delivery agents can be pharmaceutically Evaluation and Optimization of RNAi Agent:

The effectiveness of an RNAi agent can be assessed, on its ability to down-regulate the target gene expression. The evaluation can be done by contacting the RNAi agent with the cell (e.g. Mammalian cell), that has been infected with or will be infected with the virus of interest e.g. virus containing a target gene. Comparison can be done with respect to level of target gene expression, between prior to and following the contact of RNAi agent with the cell at RNA, protein or viral titer level. The level of target viral RNA or viral protein can be assessed by any of the known desired method known in the art. For example, the level of target mRNA level can be determined by Northern blot analysis, RT-PCR, etc. Western Blot Analysis, IFA etc. can be used to determine the level of protein and the virus titer can be detected by Plaque formation assay.

As described in one of the embodiments, the above designed RNAi agents were tested for their ability to inhibit the production of Chikungunya virus in mammalian cell lines. To study the effects of above designed RNAi agents, Vero E6 cell lines were seeded in 6 well plates and infected with Chikungunya virus. After 2 hrs post infection, these cells were transfected with different siRNAs. Total RNA was isolated 24 hrs after virus infection. Chikungunya virus production was detected measuring E3 RNA copies by RT-PCR. RNAi agents NIVsi-1 and NIVsi-5 showed substantially stronger inhibition of Chikungunya virus as compared to other RNAi agents, repressing Chikungunya virus by 5 $\log_{10}$ ($p<0.001$) and ~2.5 $\log_{10}$ ($p<0.05$) RNA copies respectively [FIG. 2].

The RNAi agent concentration can be optimized by testing their effects at different concentration in infected cell line. In one of the embodiments, Chikungunya virus infected Vero E6 cell lines was transfected with NIVsi-1 and NIVsi-5 RNAi agents individually and in combination at different concentrations i.e. 10, 50, 100, 150, 200 pmol. The total RNA was isolated 24 hrs after infection and Chikungunya virus was detected by measuring the E3 RNA copies by RT-PCR. RNAi agents NIVsi-1 and NIVsi-5 treatment at 10 pmol concentration failed to reduce Chikungunya virus titers whereas all other concentrations showed significant reduction in viral titers [FIG. 3A]. The reduction in Chikungunya virus copies by NIVsi-1 and NIVsi-5 reached a plateau region at 100+ pmol concentration [FIG. 3A]. Also cell viability due to addition of Hiperfect Transfection Reagent to the RNAi agent was measured by MTT assay [FIG. 3B].

Testing (In-Vitro & In-Vivo):

The RNAi agent identified can be tested by in vitro and in-vivo methods for inhibition of targeted genes by contacting the RNAi agent with the desired cell or an animal.

For example, the in vitro test is generally performed on cells or cell lines (eg. Vero E6 cell lines) infected with the desired virus by administering the RNAi agent targeting the viral genes.

In one of the embodiments, the cell line used is an mammalian cell line i.e. Vero E6 cell line. The evaluation of the RNAi agents i.e. NIVsi-1 and NIVsi-5 at 100 pmol concentration, individually and in combination was carried out using Amaxa nuleofector device. The results were evaluated at 24, 36 and 48 hrs using MTT assay.

The in vivo testing can be done by administering a virus infected animal with an RNAi agent targeting the desired viral genes. RNAi agent is evaluated on the basis of stability, biodistribution and its ability to inhibit the viral genes e.g. Chikungunya virus genes or to reduce the viral titer. The administration of the RNAi agent to an infected animal can be by any of the drug delivery routes known in the art. The RNAi agent can be directly administered to the target tissues, such as by injection or by any other suitable routes. The RNAi agent can be administered to an animal by systemic or local routes of drug administration as a means of treating viral infection.

The evaluation of the RNAi agent can be done by determining the down-regulated viral gene expression in the tested cells, cell lines or an animal. The levels of viral gene expression can be measured, for example by Quantitative RT-PCR, IFA assay or any other histopathological test known in the art. Plaque assay can be used to determine the viral titers.

In other embodiment, the animal model used is an mammal i.e. Swiss Albino mouse and C57BL/6 mouse. The RNAi agents were evaluated on Chikungunya virus infected Swiss albino and C57BL/6 mouse by injecting compositions containing NIVsi-1 and NIVsi-5 individually as well as in combination. The results (FIGS. 5 A,B,C,D) showed significant reduction in the Chikungunya virus copies.

Under certain circumstances, RNAi agent or siRNAs can induce the interferon (IFN) pathway and trigger inflammation. It has been suggested that canonical siRNA duplexes are potent activators of the mammalian innate immune system, synthetic siRNA in delivery vehicles that facilitate cellular uptake can induce high levels of inflammatory cytokines and interferons after systemic administration in mammals. To differentiate the modes of protection offered by siRNAs, expression levels of interferon α,β, and γ interferon genes in the muscle tissues of different mice groups were determined (Table 3). RNAi agents alone did not induce significant induction of interferon genes when compared to the virus infected mice. These observations revealed inhibition of Chikungunya virus was mainly because of characteristic activity of RNAi agents.

In general, the delivery of RNAi agents into the subject is done to achieve delivery of the RNAi agent to the site of infection. In one of the preferable embodiments, delivery means is administration by injection to the localized tissues.

Dosage:

RNAi agent can be administered at a dosage range of about 1 mg/kg of body weight or less than 200 pmol. The dosage range can be an amount effective to inhibit the targeted viral mRNA, viral protein or the viral titer. The dosage range can be standardised according to standard protocols to study the effects of the target molecules by any skilled person in art. The dosages can be in range of 0.1 mg to 2 mg per kg of bodyweight or can be in range of 10 to 200 pmol. The unit dose, for example can be administered by injection or by direct contact with targeted molecules. The dosage range in one of the examples is around 1 mg/kg of bodyweight of an animal. In another example, the dosage range is around In one of the embodiments, inhibition of E2 gene expression was carried out using the composition containing RNAi agent i.e Seq ID 1, along with Hiperfect transfection reagent which was transfected/injected into Chikungunya virus infected mammalian cell line (Vero E6 cell line) or a mammal (example: mouse) for the inhibition of the E2 gene of Chikungunya virus.

In another embodiment, inhibition of nsP1 gene expression was carried out using the composition containing RNAi agent i.e Seq ID 5, along with Hiperfect transfection reagent which was transfected/injected into Chikungunya virus infected mammalian cell line (Vero E6 cell line) or a mammal (example: mouse) for the inhibition of the nsP1 gene of Chikungunya virus.

In yet another embodiment, inhibition of E2 and nsP1 gene expression or reduction in Chikungunya virus viral titer was carried out using the composition containing RNAi agents i.e. both Seq ID 1 and Seq ID 5, along with Hiperfect transfection reagent which was transfected/injected into Chikungunya virus infected mammalian cell line (Vero E6 cell line) or a mammal (example: mouse) for the inhibition of the E2 gene or nsP1 gene or viral titer of Chikungunya virus. It also describes a method of inhibition of E2 and nsP1 gene expression using the above RNAi agent. The method of inhibition includes reduction in viral protein, viral mRNA or viral titer in the mammalian cell or a mammal.

The invention is further illustrated by the following examples, which should not be construed as further limiting.

EXAMPLES

Example 1

Designing of the siRNA's

All Chikungunya virus whole genotype sequences were retrieved from GenBank NCBI database. All sequences were aligned using MUSCLE software. Consensus sequence obtained from these sequences was used for designing of siRNA. All siRNAs were designed using HP OnGuard siRNA design. Four siRNAs each, targeting E2 and nsp1 genes were designed and synthesized (Qiagen, Germany). siRNAs were then checked for homology to all other sequences of the genome using non-redundant sequence database and homology analysis tool.

The siRNAs, targeted against E2 and nsP1 genes of Chikungunya virus designed according to the above procedure are given in Table 1 with other related data.

Example 2

In Vitro Evaluation

In Vitro Assay and In Vitro Infection:

For the comparison of antiviral activity of designed siRNA's, Vero E6 cell were transfected with Chikungunya virus (MOI 5; strain number 634029, African genotype). Two hours post infection, cells were transfected with siRNA targeted against E2 gene i.e. NIVsi-1, NIVsi-2, NIVsi-3, NIVsi-4 and nsP1 gene i.e. NIVsi-5, NIVsi-6, NIVsi-7, NIVsi-8 individually and control using the Amaxa Nucleofector device II (Amaxa biosystems). After electroporation, Vero E6 cells were incubated at 37 deg. C. until analyzed for inhibition of Chikungunya virus replication. Cells were harvested at 24, 36, and 48 hrs post infection and inhibition of Chikungunya virus replication was determined using by quantitative RT-PCR (qRT-PCR), Plaque assay and IFA assay.

Optimization of siRNA Concentration:

At two hours post-infection with Chikungunya virus, Vero E6 cells were transfected with NIVsi-1, NIVsi-5 individually as well as combination of both i.e. NIVsi-1 & NIVsi-5 at different concentrations i.e. 10, 50, 100, 150 and 200 pmol. After 24 h post transfection, total RNA were isolated from tissue culture supernatant and cells. One step qRT-PCR was carried out to evaluate the inhibitory effect of siRNA.

MTT Assay:

Cytotoxicity tests were performed with Vero E6 cells using an in vitro toxicology assay kit (TOX-1, Sigma) based on the reduction activity of methyl thiazolyl tetrazolium (MTT). Twenty-four hours before transfection, $5\times10^3$ cells were seeded in a 96-well plate. The transfection was performed using Hiperfect transfection reagent according to the manufacturer's instructions. The cells were divided into four groups:

1) Control group (No Hiperfect and siRNA);
2) Hiperfect group;
3) nsP1 siRNA group; and
4) E2 siRNA group.

Transfection of siRNAs was done the following day as described earlier in in vitro assay and in vitro infection section. Experiments were conducted with nontransfected or siRNA transfected (100 pmol) cells at 24 and 48 hour post-transfection. 24 hours after the siRNA transfection, the cells of the appropriate groups were subjected to MTT assay (TOX-1, Sigma). Blue formazon, solubilized by adding MTT solubilization solution to the wells, produced by viable cells was quantified in ELISA reader (Biorad, USA) at 570 nm after subtracting the background reading at 650 nm. The data were presented as the percentage of viable cell numbers in the siRNA treated and untreated control wells.

Quantitative RT-PCR:

RNA from Vero E6 cells, serum and mice tissues was extracted using QIAmp viral RNA minikit (QIAGEN, Valencia, Calif.) and trizol (Invitrogen USA) method respectively following the manufacturer's instructions. One step RT-PCR was performed in 25 μl reaction mixture containing 5 μl RNA, 12.5 μl TaqMan One-Step RT-PCR 2× Master Mix, 1 μl 40× (RT+RNAasin) (Applied Biosystems) each 1 μl sense (μM), 1 μl anti-sense (μM) primer and 1 μl TaqMan probe. Primers were selected from the E3 structural protein region. Real-time one step RT-PCR was performed in a 96-well format using 7300 real time PCR system and SDS software V 1.0.2 (Applied Biosystems). The amplification program included: reverse transcription at 48° C. for 30 min, initial denaturation at 95° C. for 10 min, and 50 cycles of denaturation (95° C. for 15 sec) and annealing and extension (60° C. for 1 min). After amplification, a melting curve was acquired to check the specificity of PCR products. Signals were normalized to the standard curve using serial dilutions of RNA synthetic transcripts. Normalized data were used to measure the number of RNA copies in infected samples according to the $\Delta\Delta C_t$ analysis. Viral titers were expressed as RNA copies per ml of serum or mg tissue. Detection limit of real time PCR was 10 copies per reaction.

Plaque Assay:

We added tenfold serial dilutions of tissue culture supernatants of infected and siRNA transfected cells to a monolayer of Vero E6 cells and the plates were incubated at 37° C. for 1 h. After incubation, the medium was replaced by overlay medium (2×MEM, 2% CMC and 10% FBS (Gibco, BRL). The plates were incubated at 37° C. for 72 h; the cells were stained with amido black and the plaques were counted.

IFA Assay:

IFA assay was carried out as described by Sudeep et al. in 'Establishment and characterization of a new *Aedes aegypti* (L.) (Diptera: Culicidae) cell line with special emphasis on virus susceptibility' published in "In Vitro Cellular & Developmental Biology—Animal" (September, 2009), Vero E6 cells were fixed with acetone and blocked with 2% BSA in phosphate buffered saline (pH 7.4) for 1 h. The cells were incubated with (1:100) mouse anti Chikungunya virus antibody followed by incubation with FITC-conjugated rabbit anti-mouse (1:500) antibodies (Invitrogen, USA). Cells were counter stained with Evan's blue for one minute. The slides were visualized using fluorescence microscope (Nikon eclipse T2000S and Q capture pro 5.0 software). Negative controls were similarly processed.

Statistical Analysis:

All data were expressed as mean±standard deviation. The viral loads were log-transformed for improvement of normality. Statistical significance was determined by Dunnet's test using ANOVA. A value of $p<0.05$ was considered statistically significant. Fold change was compared using one way ANOVA and the groups were also compared by nonparametric Kruskal-Wallis test for confirmation of results.

Results:

Four siRNAs each were designed to have an antisense strand complementary to the E2 and ns1 RNA. The sequences and the corresponding genomic positions are shown in Table 1 and FIG. 1 respectively.

Efficiency of Different siRNAs in Reducing Chikungunya Virus Replication In Vitro:

For the initial comparison of antiviral activity of different siRNAs, Vero E6 cells were infected with Chikungunya virus and transfected with different siRNAs (NIVsi-1 to NIVsi-8) 2 h post-infection. NIVsi-1 and NIVsi-5 were the most effective siRNAs, repressing Chikungunya virus by 5 $\log_{10}$ ($p<0.001$) and ~2.5 $\log_{10}$ ($p<0.05$) (FIG. 2). The reduction in Chikungunya virus copies by NIVsi-1 and NIVsi-5 was initiated at siRNA concentrations of 25 pmol, and reached a plateau at 100 pmol (FIG. 3A).

Cell Viability after siRNA Treatment (MTT Assay):

At 24 hrs post transfection compared to untreated cells, E2 siRNA (97.5±16.3), nsP1 siRNA (92.83±13.49) and Hiperfect reagent (95.88±11.47) displayed small reductions in percent viable cell numbers in vitro (FIG. 3B). Similarly at 48 hrs, transfection of E2 siRNA (76.3±9.24), nsP1 siRNA (75.79±16.69) and Hiperfect reagent (83.44±23.38) were less toxic to cells (FIG. 3B).

Effect of NIVsi-1 and NIVsi-5 siRNAs on Infections Chikungunya Virus Production:

FIG. 4A depicts the effect of NIVsi-1, NIVsi-5 and Comb-siRNAs (i.e. Chik-1 and NIVsi-5) on Chikungunya virus production at different time points. At 24 hours post infection, treatment of NIVsi-1, NIVsi-5 and comb-siRNAs resulted in the reduction of 5 $\log_{10}$, 3 $\log_{10}$ and 5 $\log_{10}$ Chikungunya virus RNA copies respectively (FIG. 4A). At 36 hours post infection, treatment of NIVsi-1, NIVsi-5 and comb-siRNAs showed 3 $\log_{10}$, 2 $\log_{10}$ and 3 $\log_{10}$ reduction in Chikungunya virus RNA copies was observed in tissue culture supernatant whereas 2 $\log_{10}$ reduction was recorded in cells with Comb-siRNAs (FIG. 4A). At 48 hours post infection, no significant reduction in Chikungunya virus RNA copies was noted in cells and supernatant.

Overall, the siRNAs directed against E2 gene (i.e. NIVsi-1) were more efficient in inhibiting Chikungunya virus production than the siRNA directed against ns1 region (i.e. NIVsi-5). We further evaluated the additive advantage of treatment with Comb-siRNAs. In supernatant, 5 $\log_{10}$ ($p<0.001$), 2.5 $\log_{10}$ ($p<0.05$) and 2.5 $\log_{10}$ (ANOVA Dunnet's test $p<0.05$) reduction in Chikungunya virus copies was observed at 24, 36 and 48 hours respectively when compared to virus infected control. In cells, 4.5 $\log_{10}$ ($p<0.001$), 3 $\log_{10}$ ($p<0.05$) and 2 $\log_{10}$ ($p<0.05$) reduction was obtained at 24, 36 and 48 hours respectively. Importantly, the Comb-siRNA could prolong the inhibitory effect as compared to individual siRNAs (FIG. 4A). NIVsi-1 and NIVsi-5 showed sequence dependent inhibition and showed no reduction in Chandipura virus replication in Vero-E6 cells (Data not shown).

When plaque assay was used as the measure of Chikungunya virus replication, NIVsi-1 siRNA yielded a reduction of 5 $\log_{10}$ at 48 hours post infection (Table 2). NIVsi-5 reduced 3 $\log_{10}$ and Combo-siRNA showed reduction of 3 $\log_{10}$ in virus titer. At 24 and 36 hours post infection, cytopathic effects were not observed in treated cultures whereas commencement of cytopathic effects was observed in untreated control from 24 hours post infection demonstrating the inhibitory effect of the siRNAs. Consistent with our real time RT-PCR results and plaque assay results, IFA also showed reduction of viral antigen in NIVsi-1 and NIVsi-5 siRNAs treated cells (FIG. 4B).

TABLE 2

Plaque assay showing inhibitory effect of siRNAs on Chikungunya virus (CHIKV) replication in Vero E6 cell line at 48 h.

| Material | Virus titer (pfu/ml) | Virus inhibition compared to virus control |
|---|---|---|
| Untreated | $4 \times 10^7$ | Nil |
| CHIKV + NIV si-1 siRNA | $2 \times 10^2$ | >5 $\log_{10}$** |
| CHIKV + NIV si-5 siRNA | $4 \times 10^4$ | 3 $\log_{10}$* |
| CHIKV + Comb-siRNA | $7.5 \times 10^4$ | ~3 $\log_{10}$* |
| CHIKV + ncsiRNA | $4 \times 10^7$ | Nil |

Values are given as mean pfu/ml.
Significance ANOVA, Dunnett's test:
*$p < 0.05$;
**$p < 0.01$.

Example 3

In Vivo Evaluation

Inhibition of Chikungunya Virus Using NIVsi-1 and NIVsi-5 siRNA:

Swiss albino and C57BL/6 mice (4-6 weeks) were infected with approximately $1\times10^6$ PFU of Chikungunya virus (100 μl of $10^7$ pfu/m; ~$4.5\times10^8$ RNA copies/ml;) i.v. and RNA copies were checked daily in blood and muscles by one step qRT-PCR for seven days. siRNAs were complexed with HiPerfect™ (QIAGEN, Valencia Calif.) according to the manufacturer's instructions and ~25 μg/mouse (1 mg/Kg body wt) was administered i.v. once after 72 h post infection. NIVsi-1 siRNA, NIVsi-5 siRNA and combination of NIVsi-1 and NIVsi-5 siRNAs (Comb-siRNA) were used in different mice groups. Blood (~200 μl) was collected from siRNA, ncsiRNA, or saline injected mice groups at 0, 1, 2, 3 and 4 day post treatment. Chikungunya virus E3 RNA was quantitated from sera using qRT-PCR. In C57BL/6 mice only 72 hours time point was chosen for siRNA treatment. Blood and hind limb muscle tissues were harvested from C57BL/6 mice at 0, 1, 2, 3 and 4 day post siRNA injection. The tissues were dissected, weighed, crushed and macerated in liquid nitrogen using mortar pestle, and further used for RNA isolation.

Quantitative RT-PCR:

RNA from Vero E6 cells, serum and mice tissues was extracted using QIAmp viral RNA minikit (QIAGEN, Valencia, Calif.) and trizol (Invitrogen USA) method respectively following the manufacturer's instructions. One step RT-PCR was performed in 25 μl reaction mixture containing 5 μl RNA, 12.5 μl TaqMan One-Step RT-PCR 2× Master Mix, 1 μl40× (RT+RNAasin) (Applied Biosystems) each 1 μl sense (μM), 1 μl anti-sense (μM) primer and 1 μl TaqMan probe. Primers were selected from the E3 structural protein region. Real-time one step RT-PCR was performed in a 96-well format using 7300 real time PCR system and SDS software V 1.0.2 (Applied Biosystems). The amplification program included: reverse transcription at 48° C. for 30 min, initial denaturation at 95° C. for 10 min, and 50 cycles of denaturation (95° C. for 15 sec) and annealing and extension (60° C. for 1 min). After amplification, a melting curve was acquired to check the specificity of PCR products. Signals were normalized to the standard curve using serial dilutions of RNA synthetic transcripts. Normalized data were used to measure the number of RNA copies in infected samples according to the $\Delta\Delta C_t$ analysis. Viral titers were expressed as RNA copies per ml of serum or mg tissue. Detection limit of real time PCR was 10 copies per reaction.

Plaque Assay:

We added tenfold serial dilutions of tissue culture supernatants of infected and siRNA transfected cells to a monolayer of Vero E6 cells and the plates were incubated at 37° C. for 1 h. After incubation, the medium was replaced by overlay medium (2×MEM, 2% CMC and 10% FBS (Gibco, BRL). The plates were incubated at 37° C. for 72 h; the cells were stained with amido black and the plaques were counted.

IFA Assay:

IFA was carried out as described by Sudeep et al. [29], Vero E6 cells were fixed with acetone and blocked with 2% BSA in phosphate buffered saline (pH 7.4) for 1 h. The cells were incubated with (1:100) mouse anti Chikungunya virus antibody followed by incubation with FITC-conjugated rabbit anti-mouse (1:500) antibodies (Invitrogen, USA). Cells were counter stained with Evan's blue for one minute. The slides were visualized using fluorescence microscope (Nikon eclipse T2000S and Q capture pro 5.0 software). Negative controls were similarly processed.

Histopathology:

Hind limb tissues, not including the femur, were fixed in 4% formaldehyde and were embedded in paraffin and 8 μm sections were prepared. Tissues were stained with haematoxylin and eosin. Histopathological evaluation was performed on muscle tissues of hind legs from control (saline injected, ncsiRNA), chikungunya infected (4, 5, 6 and 7 day post infection), treatment groups (NIVsi-1 siRNA, NIVsi-5 siRNA and Comb-siRNA). siRNA treatment was given on third ND and tissues were harvested at 4, 5, 6 and 7 PID and evaluated for necrosis, inflammation, regeneration, mineralization, fibrosis and edema. Similarly IFA was carried out to check the presence of Chikungunya virus. IFA was carried out as described by Sudeep et al, The slides were incubated with (1:100) mouse anti Chikungunya virus antibody followed by incubation with Alexa flor 546-conjugated rabbit anti-mouse. (1:200) antibodies (Invitrogen USA). Cells were counter stained with DAPI for 10 seconds. The slides were visualized using fluorescence microscope (Nikon eclipse T2000S and Q capture pro 5.0 software). Negative controls were similarly processed.

Interferon Gene Expression Analysis Employing Real Time PCR:

For real-time reverse transcription RT-PCR analysis, hind limb muscle tissues were crushed in liquid nitrogen. RNA was extracted by using TRIzol reagent (Invitrogen) according to the manufacturer's instructions. One step RT-PCR was performed using Quantitect SYBR Green RT PCR kit (Qiagen, Hilden, Germany). Real-time PCR analysis used the following nucleotide primers:

```
                                        (Seq ID 17)
5'-GGCCGAGGACTTTGATTGCACATT-3'
and

                                        (Seq ID 18)
5'-AGGATGGCAAGGGACTTCCTGTAA-3' for actin beta,

                                        (Seq ID 19)
5'-AGGAGGAGTTTGATGGCAACCAGT -3'
and

                                        (Seq ID 20)
5'-TCCTCATCCCAAGCAGCAGATGAA-3' for Interferon
alpha (INF-a),

                                        (Seq ID 21)
5'-TGTGGCAATTGAATGGGAGGCTTG-3'
and
```

-continued

```
                                        (Seq ID 22)
5'-TCTCATAGATGGTCAATGCGGCGT-3' for inter-
feron beta
(IFN-p),
and

                                        (Seq ID 23)
5'-AGCGGCTGACTGAACTCAGATTGT-3'
and

                                        (Seq ID 24)
5'-ACTGCTTTCTTTCAGGGACAGCCT-3' for interferon
gamma (IFN-y).
```

The 25 μl amplification reaction mixture contained 500 ng total RNA, 0.5 μM each primer pair, 0.25 of reverse transcriptase enzyme and 12.5 μl of 2×SYBR green qPCR Supermix (Quiagen).

Cycling conditions were as follows: one cycle of 50° C. for 30 min and one cycle of 95° C. for 15 min followed by 45 cycles of 94° C. for 15 s, 57° C. for 30 s, 72° C. for 30 s and 68° C. for 15 s. The real-time PCR was performed by using a Rotor-Gene 3000 PCR machine. The data were analyzed with Rotor-Gene real-time analysis software. Each sample was analyzed in duplicate and normalized to actin beta mRNA. Expression changes in interferon alpha, beta, and gamma genes in chikungunya infected group, chikungunya infected mice with NIVsi-1, NIVsi-5 and Comb-siRNA treatment group, and control mice with NIVsi-1, NIVsi-5 and Comb-siRNA treatment were investigated using real time PCR analysis. Mice were mock-infected with CHIKV and treated with siRNA at day 3 and then gene expression determined at days 4, 5, 6 and 7. Three mice were used for each treatment and time point.

Statistical Analysis:

All data were expressed as mean±standard deviation. The viral loads were log-transformed for improvement of normality. Statistical significance was determined by Dunnet's test using ANOVA. A value of $p<0.05$ was considered statistically significant. Fold change was compared using one way ANOVA and the groups were also compared by nonparametric Kruskal-Wallis test for confirmation of results.

Results:

Swiss Albino and C57 BL/6 Mice are Permissive to Chikungunya Virus Infection:

Infection of adult Swiss albino and C57BL/6 mice with $1\times10^6$ PFU Chikungunya virus (100 μl of $10^7$ pfu/ml). Chikungunya virus by intravenous route did not cause mortality or clinical symptoms. However, definite evidence of the replication of the virus was observed. Chikungunya virus RNA copies were detected in mice serum from 1 PID till 7 PID. Viremia in i.v. inoculated mice reached a peak by 3 days post inoculation (dpi), with viral loads ranging from $7\times10^5$ to $5\times10^7$ viral RNA copies/ml (FIG. 5).

siRNA Inhibits the Chikungunya Virus Replication in Swiss Albino Mice:

To assess whether siRNAs could protect mice from Chikungunya virus infection, groups of Chikungunya virus infected mice ($1\times10^6$ PFU Chikungunya virus; 100 μl of $10^7$ pfu/ml) were administered NIVsi-1 and NIVsi-5 siRNAs at 72 hours post infection. Swiss albino mice treated with E2' or nsP1 siRNA with 250 μg per kg body weight (~6 μg/mice) showed ~3 $\log_{10}$ inhibition, 500 μg per kg body weight (~12 μg/mice) showed 3 $\log_{10}$ inhibition of Chikungunya virus whereas at 1 mg per kg body weight (~25 μg/mice) siRNA led to 7 $\log_{10}$ reduction in Chikungunya virus copies (FIGS. 5A & B). Similar results were obtained in C57BL/6 mice (FIGS. 5C & D). We therefore administered 1 mg kg body weight (~25 µg/mice) siRNA in subsequent experiments. For all in-vivo experiments, Hiperfect reagent was used for delivery of siRNA. NIVsi-1, NIVsi-5 and Comb-siRNA administered at 72 h post infection provided significant reduction in serum viral load as assessed by real time PCR (FIG. 6). At 48 h post siRNA injection, reduction with NIVsi-1 and NIVsi-5 was around 2.5 $\log_{10}$ (ANOVA Dunnet's test $p<0.05$) as compared to 0 h and ncsiRNA whereas 100% inhibition (7 $\log_{10}$) was observed with Comb-siRNA (ANOVA Dunnet's test $p<0.01$). At 72 h post-virus infection, administration of NIVsi-1, NIVsi-5 and Comb-siRNAs showed complete inhibition (7 $\log_{10}$ ANOVA Dunnet's test $p<0.01$).

Inhibition of the Chikungunya Virus Replication in C57BL/6 Mice after Treatment of siRNA:

NIVsi-1, NIVsi-5 and Comb-siRNA administered 72 h post Chikungunya virus infection ($1\times10^6$ PFU Chikungunya virus; 100 µl of $10^7$ pfu/ml) provided significant reduction in serum viral load as assessed daily by real time PCR (FIG. 7). At 24 h and 48 h post siRNA treatment, 2.5 $\log_{10}$ and 3.5 $\log_{10}$ (ANOVA Dunnet's test $p<0.05$) reduction was recorded for all siRNAs, when compared to ncsiRNA. At 72 h post treatment, reduction with siRNA NIVsi-1, and NIVsi-5 was around 3.5 $\log_{10}$ (ANOVA Dunnet's test $p<0.05$) while Comb-siRNA showed 100% inhibition (7 $\log_{10}$, ANOVA Dunnet's test $p<0.01$). Importantly, Comb-siRNA produced prolonged inhibitory effect when compared to individual siRNAs. In muscle tissues, Chikungunya virus RNA reached peak by third post-day infection (PID), with viral loads ranging from $1\times10^4$ to $7\times10^5$ viral RNA copies/mg tissue (FIG. 7). At 24 h post-siRNA treatment ~2.5 $\log_{10}$ reduction in Chikungunya virus RNA was noted with all the three siRNAs as compared to ncsiRNA control. At 72 h, all the siRNAs produced 4 $\log_{10}$ reduction in Chikungunya virus RNA (100% inhibition, ANOVA Dunnet's test $p<0.01$). Similar results were seen when IFA was used to evaluate the effect of siRNA on Chikungunya virus replication in muscle tissues that corroborated with real time PCR-based data (FIG. 8).

Histopathological Evaluation of Mice Muscle Tissues after Chikungunya Virus Infection and siRNA Treatment:

Having demonstrated that NIVsi-1 and NIVsi-5 siRNA treatment significantly reduced the Chikungunya virus titer in serum and muscle tissues, histopatholgical analysis was performed to determine the inflammation and infiltration in Chikungunya infected and siRNAs treated tissues. Histopathological examination of Chikungunya virus infected mice ($1=10^6$ PFU Chikungunya virus; 100 µl of $10^7$ pfu/ml) showed pathological changes such as extensive necrosis, inflammation, pronounced monocyte/macrophage infiltrates and edema (FIG. 9). Such histopathological changes were prevented by systemic treatment either with NIVsi-1, NIVsi-5 individually or in Comb-siRNAs. At 4 PID, Chikungunya infected mice muscle tissues showed moderate inflammation of lymphocytes and monocytes, focal edema and focal necrosis whereas siRNA treated mice muscle tissues showed only mild inflammation. At 7 PID, extensive muscular necrosis with dense inflammation of lymphocytes and monocytes was observed in Chikungunya virus infected and ncsiRNA treatment mice. On other hand, siRNA treatment preserved the morphological integrity of the muscle tissues with regeneration (FIG. 9). The muscle tissues from control mice infected with saline showed no pathological changes such as necrosis, edema, inflammation and infiltration of polymorphs (FIG. 9).

Expression Levels of Interferon Genes after siRNA Treatment:

We tested if inhibition of Chikungunya virus replication in mice was indeed sequence dependent and not because of non-specific antiviral interferon response. In the absence of Chikungunya virus, NIVsi-1, NIVsi-5 and Comb-siRNA treatment did not significantly induce α, β, γ interferon mRNA expression (Table 3; Kruksal Wallis $p>0.05$). Similarly, siRNA treatment of Chikungunya virus-infected mice did not show significant elevations in α, β, γ interferon gene expression (Table 3; Kruksal Wallis $p>0.05$). These results suggest that siRNA mediated reduction in Chikungunya virus replication is sequence specific without any deleterious effect on host.

Taken together, this first in vivo experiment clearly revealed that siRNA therapy is effective in vivo by reducing clinical symptoms in challenge-infected animals and was capable of significantly reducing viral replication in the serum and muscles.

TABLE 3

Interferon response in C57BL/6 mice after treatment with siRNAs

| | Treatment | | | Relative fold change compared to control | | |
|---|---|---|---|---|---|---|
| Post infection period | CHIKV infection | NIV si-5 siRNA | NIV si-1 siRNA | Interferon α Mean (SD) | Interferon β Mean (SD) | Interferon γ Mean (SD) |
| 4 PID | + | | | 0.94 (0.88) | 2.03 (1.31) | 25.22 (21.12) |
| | + | + | | 2.83 (2.19) | 1.81 (1.61) | 8.25 (5.06) |
| | + | | + | 2.06 (1.77) | 2.69 (2.21) | 18.00 (16.80) |
| | + | + | + | 1.21 (0.80) | 3.99 (3.82) | 4.55 (1.23)* |
| | | + | | 1.54 (1.21) | 5.18 (3.17) | 1.09 (0.60) |
| | | | + | 0.95 (0.66) | 4.76 (3.23) | 1.08 (0.64) |
| | | + | + | 2.19 (0.46) | 6.00 (4.55) | 7.09 (5.18) |
| 5 PID | + | | | 0.11 (0.05) | 0.41 (0.33) | 371.73 (236.04) |
| | + | + | | 1.88 (1.48) | 1.71 (1.54) | 19.44 (11.93) |
| | + | | + | 4.65 (2.08) | 4.74 (4.14) | 44.38 (41.70) |
| | + | + | + | 0.81 (0.30) | 3.59 (3.49) | 163.09 (65.36)* |
| | | + | | 1.22 (0.53) | 4.69 (1.06) | 3.31 (1.91) |
| | | | + | 0.60 (0.44) | 6.54 (0.74) | 0.97 (0.06) |
| | | + | + | 3.38 (2.63) | 5.55 (4.75) | 1.49 (2.00) |

TABLE 3-continued

Interferon response in C57BL/6 mice after treatment with siRNAs

| | Treatment | | | Relative fold change compared to control | | |
|---|---|---|---|---|---|---|
| Post infection period | CHIKV infection | NIV si-5 siRNA | NIV si-1 siRNA | Interferon α Mean (SD) | Interferon β Mean (SD) | Interferon γ Mean (SD) |
| 6 PID | + | | | 2.15 (2.05) | 0.42 (0.27) | 9.37 (5.87) |
| | + | + | | 2.50 (1.27) | 3.61 (3.06) | 6.06 (4.64) |
| | + | | + | 14.27 (9.47) | 1.54 (1.35) | 50.74 (42.74) |
| | + | + | + | 5.15 (4.80) | 4.85 (2.20) | 344.23 (294.86) |
| | | + | | 0.45 (0.10) | 4.89 (3.59) | 1.10 (0.74) |
| | | | + | 0.62 (0.42) | 5.71 (1.40) | 0.68 (0.65) |
| | | + | + | 3.67 (3.47) | 6.16 (5.59) | 0.78 (0.64) |
| 7 PID | + | | | 0.67 (0.56) | 2.23 (1.90) | 4071.74 (705.74) |
| | + | + | | 2.36 (1.98) | 0.54 (0.05) | 7.51 (1.50) |
| | + | | + | 18.10 (13.29) | 6.44 (5.12) | 2.15 (1.87) |
| | + | + | + | 1.32 (1.31) | 4.83 (0.33) | 119.31 (91.42) |
| | | + | | 0.58 (0.07) | 2.67 (0.18) | 1.13 (0.17) |
| | | | + | 0.52 (0.02) | 6.35 (3.68) | 2.39 (0.28) |
| | | + | + | 2.17 (1.53) | 5.74 (5.13) | 27.38 (20.14) |

Mice were treated with siRNA and gene expression changes in interferon alpha, beta and gamma was monitored at 24 h, 48 h, 72 h and 96 h post injection. Results expressed as $2^{-\Delta\Delta CT}$ were reported as mean ± standard deviation and were analyzed using Kruksal Wallis test.

*$p < 0.05$ significantly different gene expression change as compared to chikungunya infected mice of respective time point.

Advantages of the Present Invention are:

1) The RNAi agent i.e. NIVsi-1 and NIVsi-5 siRNAs when administered individually were able to inhibit the E2 and nsP1 gene of Chikungunya virus; thereby inhibiting the Chikungunya virus replication in the virus-infected mice after 72 h post-virus inoculation.

2) Comb-siRNAs (i.e. NIVsi-1 and NIVsi-5 siRNAs) provide an excellent therapeutic agent for Chikungunya.

3) Single intravenous inoculation of the siRNAs, 72 h after Chikungunya virus infection could completely inhibit Chikungunya virus replication as evidenced by the absence of viral RNA in the muscles and serum.

We claim:

1. An RNAi agent for inhibition of Chikungunya virus, particularly by targeting the E2 gene or nsP1 gene of the Chikungunya virus, comprising either:

a) a sense strand having 15-30 contiguous nucleotides as set forth in SeqID 1; and b) an antisense strand having 15-30 contiguous nucleotides as set forth in SeqID 9 complementary to said sense strand for inhibition of E2 gene of Chikungunya virus; or a) a sense strand having 15-30 contiguous nucleotides as set forth in SeqID 5; and b) an antisense strand having 15-30 contiguous nucleotides as set forth in SeqID 13 complementary to said sense strand for inhibition of nsP1 gene of Chikungunya virus.

2. The RNAi agent as claimed in claim 1, wherein said agent is an siRNA.

3. The RNAi agent as claimed in claim 1, wherein each sense and antisense strand is a 21 nucleotide long sequence.

4. A composition comprising:

a) an RNAi agent as claimed in claim 1 or a combination thereof; and b) a pharmaceutically acceptable carrier.

5. A method of reducing the level of E2 protein or nsP1 protein of Chikungunya virus, or viral titre, in cells or tissues, comprising contacting the said cell or tissue with RNAi composition as claimed in claim 4.

6. The RNAi agent as claimed in claim 1, wherein each sense and antisense strand is an 18 nucleotide long sequence.

7. The RNAi agent as claimed in claim 1, wherein each sense and antisense strand is a 19 nucleotide long sequence.

8. The RNAi agent as claimed in claim 1, wherein each sense and antisense strand is a 20 nucleotide long sequence.

9. The RNAi agent as claimed in claim 1, wherein each sense and antisense strand is a 22 nucleotide long sequence.

* * * * *